United States Patent [19]

Riethmuller et al.

[11] 4,091,416

[45] May 23, 1978

[54] APPARATUS FOR DISPLAYING A SECTION OF A BODY SUBJECTED TO PENETRATING RADIATION, IN PARTICULAR X RAYS OR GAMMA RAYS

[75] Inventors: Jacques Riethmuller; Jean Pierre Vasseur, both of Paris, France

[73] Assignee: Thomson-CSF, Paris, France

[21] Appl. No.: 611,685

[22] Filed: Sep. 9, 1975

[30] Foreign Application Priority Data

Sep. 13, 1974 France .................................. 74 31148

[51] Int. Cl.² ................................................ H04N 7/18
[52] U.S. Cl. ..................................... 358/111; 250/272; 358/903
[58] Field of Search ......... 178/6.8, DIG. 5, DIG. 16; 358/73, 111, 110, 242, 903; 315/367; 250/272, 273

[56] References Cited

U.S. PATENT DOCUMENTS

3,778,614 12/1973 Hounsfield ............................. 250/362
3,794,762 2/1974 Zukerman ............................. 358/110

Primary Examiner—Howard W. Britton
Attorney, Agent, or Firm—Cushman, Darby & Cushamn

[57] ABSTRACT

An apparatus for producing displays in the form of areas of well-defined illumination levels, in order to display a body subjected to penetrating radiation, and in particular X rays or gamma rays is provided. In this apparatus, the image is divided into two regions, the first corresponding to a narrow range of levels and the second, to a much larger range of levels. Means are provided in order to clearly differentiate the respective appearances of these two regions.

7 Claims, 11 Drawing Figures

APPARATUS FOR DISPLAYING A SECTION OF A BODY SUBJECTED TO PENETRATING RADIATION, IN PARTICULAR X RAYS OR GAMMA RAYS

In certain techniques and in particular X ray or gamma ray examination techniques, computers associated with digital-analogue converters are employed in order to display a "map" of a region of the human body which is under examination. When the region being examined is fairly uniform, the details of this map are difficult to observe. In particular, examination of the brain shows up certain regions in which opacity is a normal characteristic and other in which the degree of opacity is characteristic of a lesion, for example a tumour. It is precisely such tumours which it is the purpose of the examination to reveal.

The object of the present invention is a display apparatus which enables this problem to be resolved in a simple manner.

The display apparatus in accordance with the invention is of the kind which can display a right section of the body being studied, by means of areas whose brilliance is a function of the corresponding opacity.

It comprises essentially means for selecting zones whose opacity falls within predetermined limits selected by the operator, and for differentiating the appearance of the corresponding areas in relation to the surrounding areas.

The invention will be better understood from a consideration of the ensuing description and by reference to the attached drawings in which.

Figure 1:
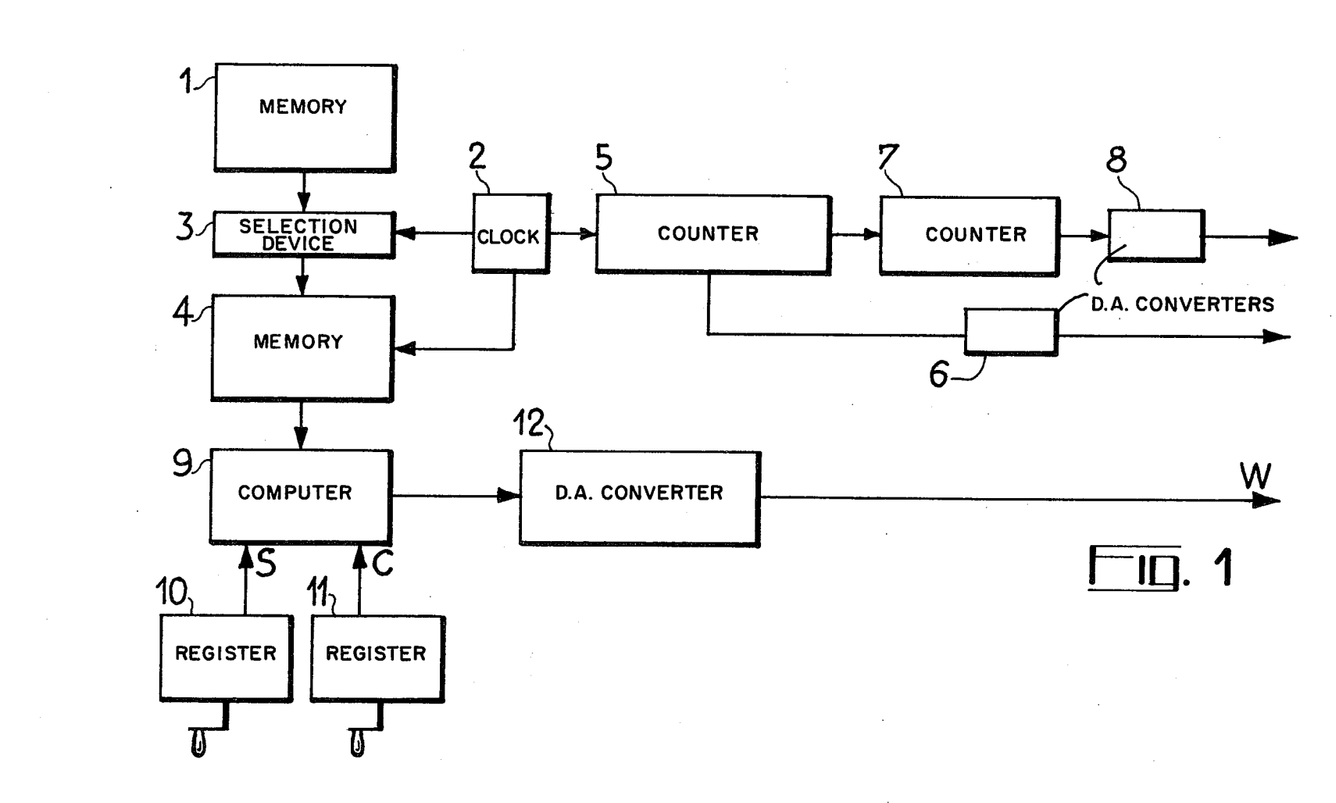
FIG. 1 is the diagram of an embodiment of that part of the apparatus to which the invention contributes an improvement.

In the FIG. 1, the reference 1 illustrates the memory in which there are recorded page by page, the assembly of results furnished by a computer (not shown) and giving for example the opacities, vis-a-vis incident radiation, for example X rays, each cross section (each page corresponding to a cross section) of a body subjected to said radiation. A clock 2 controls on the one hand a selecting device 3 which feeds the data corresponding to a page into a memory 4, in the rhythm controlled by the clock.

The clock 2, on the other hand, controls a first counter 5 which, by means of a digital to analog converter 6, controls the scanning of each line off the screen or of the semi-conductive target of a cathode-ray tube (not shown), indeed by methods well known per se in synchronism with the read-out of a line from the memory 4, the latter taking the form of a matrix of memory points.

The counter 5 in turn controls a counter 7 which, through by means of a digital-analogue converter 8, controls the line-by-line scanning of the screen of the cathode ray tube, synchronously with the reading out of the successive lines from the matrix.

The memory 4, still under the control of the clock, feeds it line-by-line into a computer 9, and each line point-by-point. To simplify the explanation, it will be assumed that computing takes place using the binary code and that the numbers representing respective opacities, range from 0 to N, N being equal to $2^P - 1$.

The computer 9 has two inputs S and C for control purposes, the function of which will be explained making reference to FIG. 2.

One of these inputs, S, is controlled by a register 10, the "threshold register", and the other C by a register 11, the "contrast" register.

These two registers respectively record two numbers, S and C, chosen by the operator, one of which is a threshold number and the other number of which serves to regulate the image contrast.

The computer 9 controls by means of a digital-analogue converter 12 the modulating electrode of the tube, and makes it possible to regulate the intensity of the electron beam.

Figure 2:
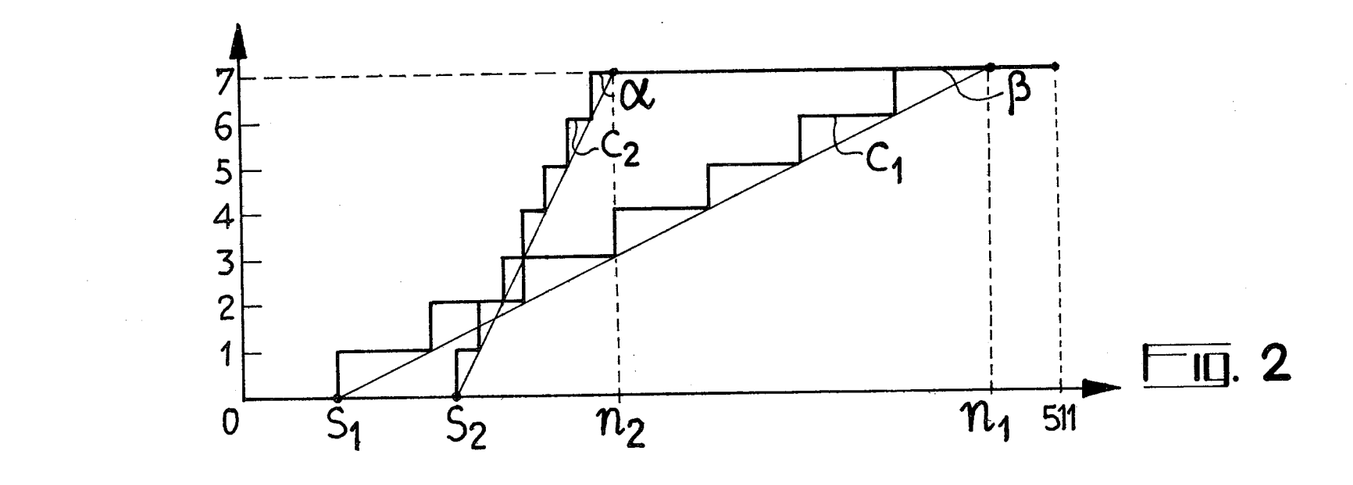
FIG. 2 is an explanatory diagram.

The operation of the system will be understood from a consideration of the graphs shown in FIG. 2.

It should be borne in mind initially, however, that on an oscilloscope screen displaying spots which vary from black through to white, the eye can only readily distinguish a limited number of grey levels, in the order of about 10 in fact. For the sake of convenience, a number of levels equal to 8 will be chosen for discussion here. The level 0 corresponds to minimum opacity and zero intensity on the electron beam of the display tube, whilst the level 7,($2^3 - 1$) corresponds to maximum opacity, that of the bones if it is a region of the human body which is being examined.

The computer 9, from the numbers comprised between 0 and N, ($2^P - 1$) and in order to provide a concrete example 511(512 − 1) generates steps ranging between 0 and 7 and each corresponding to a grey level. The graphs of FIG. 2 illustrate on the abscissa the numbers stored in the memory 4 and representing the opacities recorded at each memory point, said numbers ranging between 0 and 511, whilst on the abscissa there are plotted the output voltages from the converter 12, which represent the grey levels.

The register 10 records a number S which is a threshold below which the numbers fed out from the computer give the level 0. As seen earlier on, this threshold can be adjusted by the operator.

A register 11, which can also be adjusted, regulates the contrast of the image, that is to say the length of each step of the stepped function representing the grey levels as a function of the numbers comprised between the number representing the threshold and 511 which is the white level.

Figure 3:
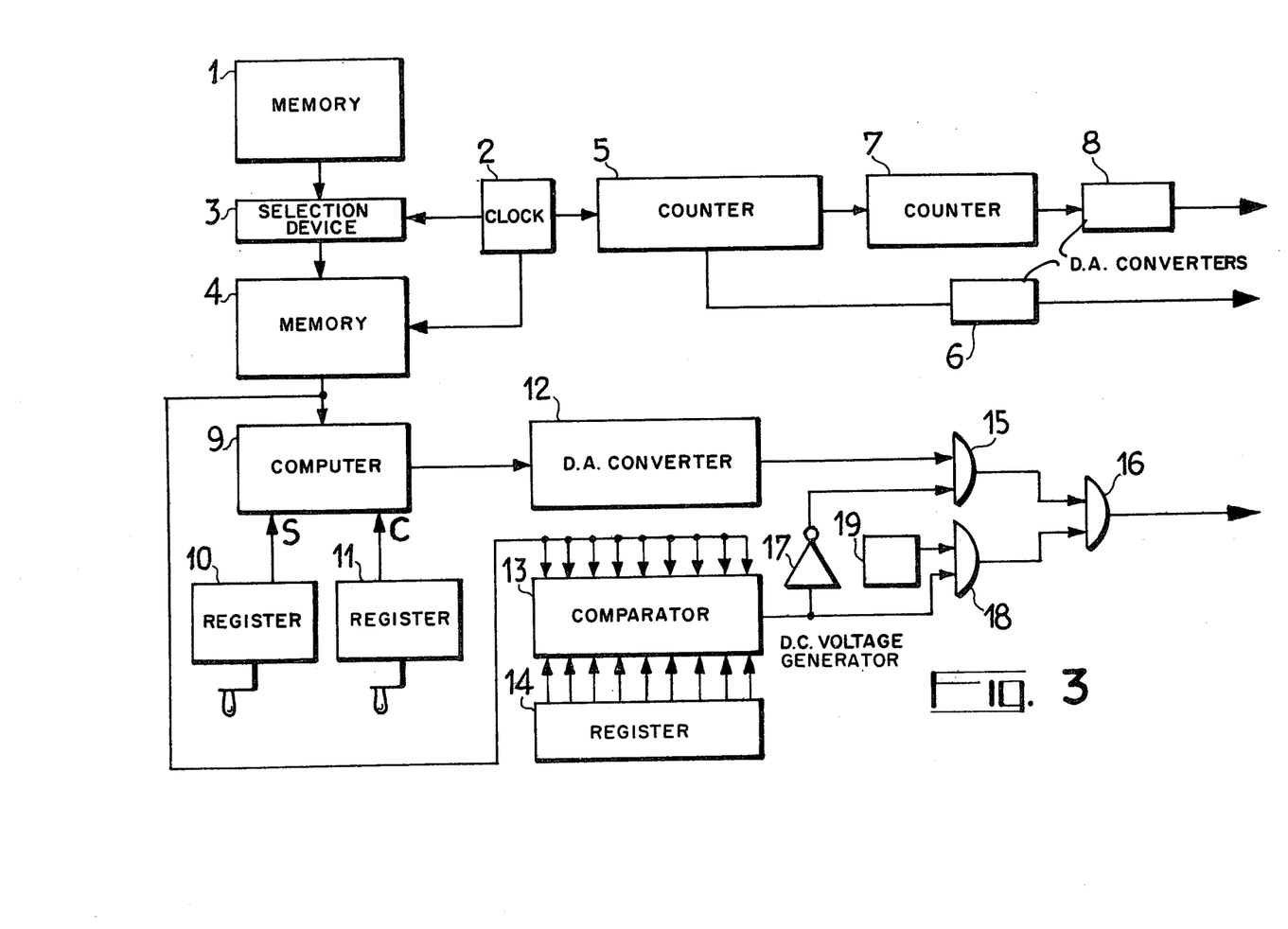
FIGS. 3, 6, 9 and 10 are diagrams of non-limitative embodiments of the invention.

The clock therefore synchronizes scanning with read-out of the memory. Each point is in reality a mesh of a matrix and each line is a succession of points, that is to say a rectangle of given height. This being the case, the foregoing system having been described purely by way of example and in order to enable the invention to be understood, FIG. 3 shows a non-limitative example of a first embodiment utilising the system of FIG. 1 as its basis but in which the inherent elements could be utilised in an equivalent system yielding the same results and known from the prior art. This system, as well as the ones described hereinafter, comprises inherent elements which form the object of the invention.

This device makes it possible to select from among the opacity levels recorded in the memory, a certain range comprised between given limits, and to represent the meshes having these opacities, in black or in white.

The device shown in FIG. 3 comprises elements identical with those of FIG. 1, which have been marked by the same references. It furthermore comprises a comparator 13 having P, i.e. 9, first inputs connected to the outputs of the memory 4, the respective states 0 and 1 of which outputs translate a number ranging between 0 and 511. It furthermore comprises 9 second inputs whose states are determined by a register 14 adjusted by the operator, representing the number between 0 and 511, and corresponding to the chosen opacity. The comparator 14 has one output normally at the logic level 0 and acquires the level 1 when the two selected numbers, the first of which issuing from the page and the second from the register 14 coincide. The converter 12 is connected to an analogue gate 15 whose outputs supply the first input of an OR-gate 16, likewise of analogue type, whose own output is connected to the modulating electrode of the cathode ray tube. The output of the comparator 13 is connected by means of an inverter 17 to the control input of the gate 15. It is connected on the other band to the control input of a second analogue gate 18 whose output is connected to the second input of the OR-gate 16. The analogue input of this second gate is connected to a d.c voltage generator 19 which, depending upon the selected operation mode furnishes either a voltage producing a black deeper than the first step, or a white higher than the last step.

Figure 5:
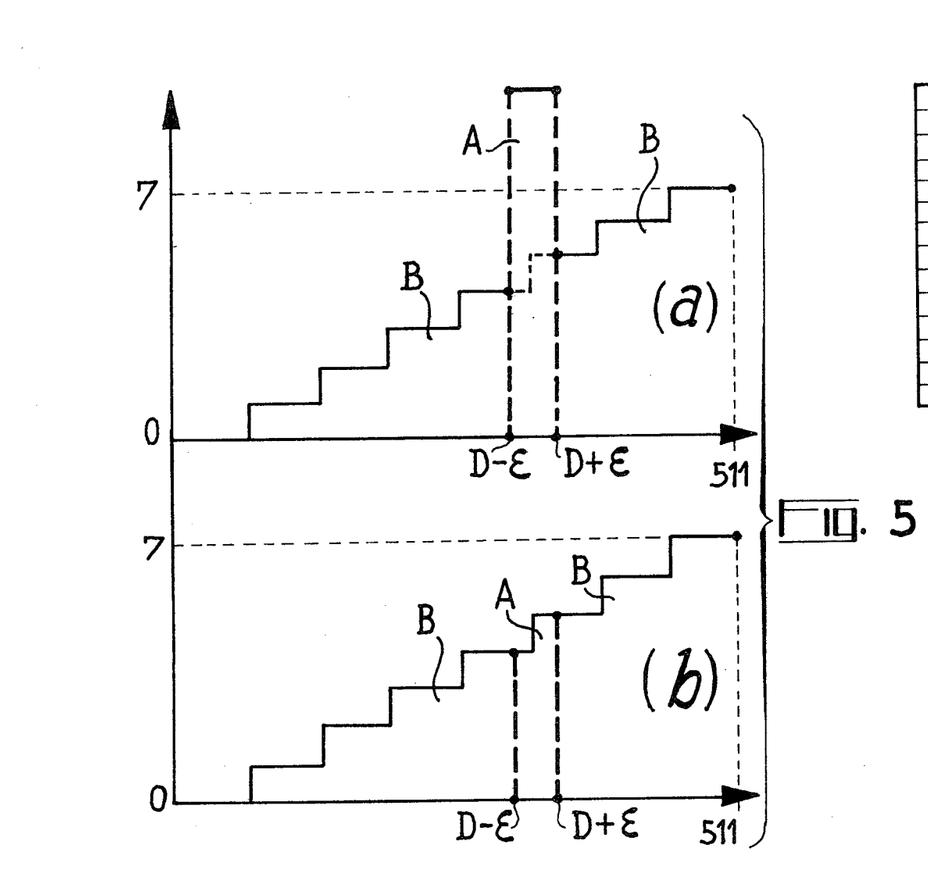
FIGS. 5, 7, 8 and 11 are respective explanatory diagrams.

Operation of the system will be understood from a consideration of FIG. 5. If the output of the comparator is in the 0 state, the gate 15 will be open by the inverter 17, and the OR-gate will furnish the step generated by the computer.

When the output of the comparator is in the 1 state, that is to say when the number chosen by the operator is recorded in the register 14 and coincides with the number fed out from the memory, the gate 18 is opened by the comparator which acquires the 1 state, and the gate 16 is open, the gate 15 is closed and the generator 19 supplies its d.c output voltage to the modulating electrode.

Figure 4:
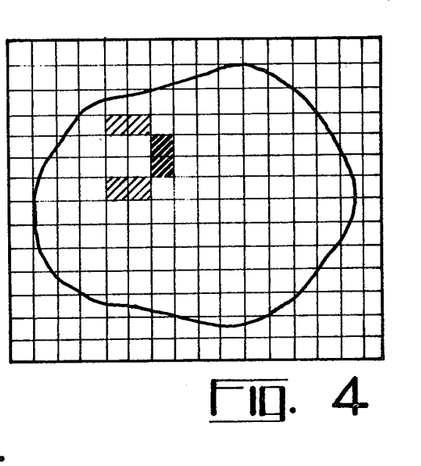
FIG. 4 is an example of the appearance of a right section obtained for instance by the device shown in FIG. 3.

In actual fact, considering FIG. 5, the operator selects a range of opacities, that is to say numbers on the horizontal scale, corresponding to one or more grey levels. FIG. 5A corresponds to representation by a level which is whiter than white. FIG. 5B corresponds to a level which is blacker than black. FIG. 4 illustrates the result obtained in the latter case, which is a case of special display. The region A is the selected region.

Figure 6:
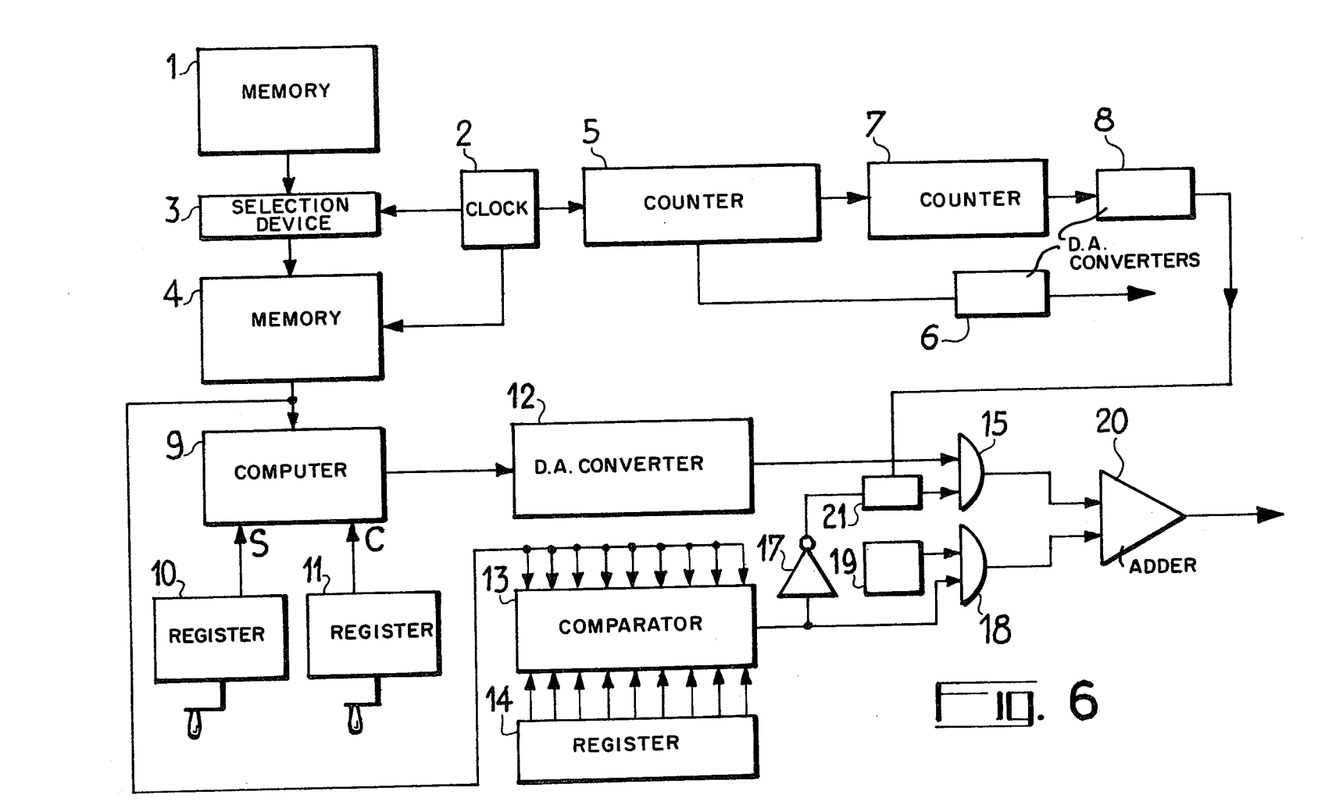

FIG. 6 shows another embodiment of the invention. The essential elements of this figure are the same as those of FIG. 3, with the exception of the following differences:

The OR-gate 16 is replaced by an adder 20 and a squarewave generator 21, synchronised with the line scan function, is inserted between gate 15 and inverter 17.

Figure 7:
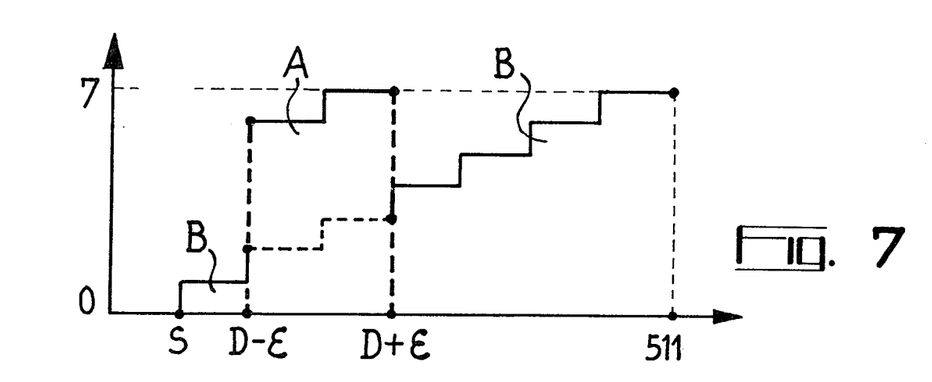

The operation of the system will be understood from a consideration of FIG. 7.

When the number issued from the memory 4 is equal to the number selected by the operator, the d.c voltage furnished by the generator 19 is added in the adder 20 to the voltage furnished by the converter 12. The inverter 17 starts the squarewave generator 21 which, when it delivers its highest voltage, opens the gate 15 and closes this gate, when it delivers its zero voltage. Thus, two effects are obtained: on the one hand, when the selected number is recorded by the memory, the voltage furnished by the modulating electrode changes to a very much higher level. On the other hand, when the number is not recorded, the generator 21 causes the meshes to flash, with the exception of those corresponding to the chosen opacity.

In the two former cases, it has been assumed that the comparator 13 acquired the 1 state when all the significant digits of the two numbers, that is to say that chosen by the operator and that issued from the memory 4, coincide. It is more often of interest to choose an opacity range, that is to say to give the representative number a lower limit and a upper limit. The comparator 13, by methods known to the person skilled in the art, can be designed to achieve this result and an example of this will be given in addition, at a later point.

Figure 9:
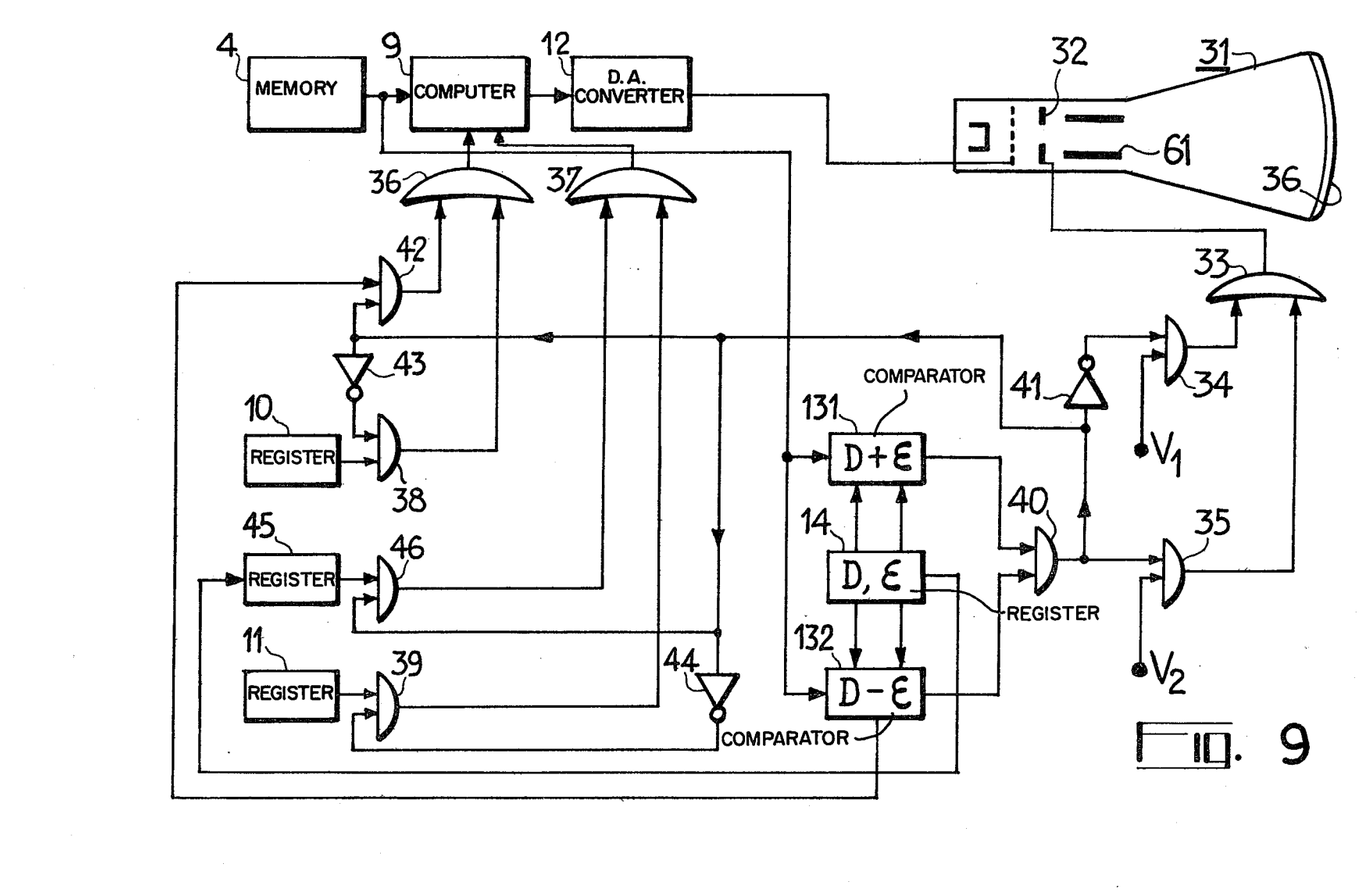

FIG. 9 illustrates another embodiment of the invention.

In this new embodiment, the zone which it is required to differentiate, will appear upon a cathode ray tube in a colour and with a contrast, differing from the remainder of the image.

In this device, for example a cathode ray tube with two kinds of phosphorus will be used, each of which is made to fluoresce by a given acceleration voltage. For example, for a voltage $V_1$ applied to the anode, a red phosphorus will be excited, and for a voltage $V_2$, a green phosphorus.

Figure 8:
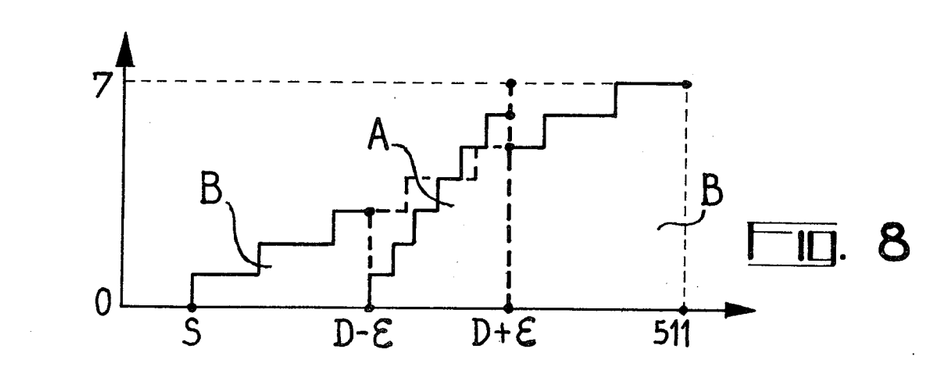

Before describing this example, the diagram of FIG. 8 will be considered. In this diagram, the object in mind is to differentiate the opacities corresponding to a range comprised between the limits $D - \epsilon$, $D + \epsilon$, where D and $\epsilon$ are chosen at will by the operator. In this range, there will be encountered on the screen the same brilliance levels as for the remainder of the image. The remainder of the image will have the same brilliance levels, the contrast $C_B$ and the threshold S being chosen previously as in the earlier examples.

The colour of this part B will for example be green. The region A comprised between $D - \epsilon$, $D + \epsilon$ will have a much higher contrast $C_A$ than the contrast $C_B$ and will commence from the threshold $D - \epsilon$, at the level 0, working up to the level 7 at $D + \epsilon$, but the corresponding points or meshes will be red.

In FIG. 9, neither the clock nor the tube scanning circuits have been illustrated. Instead, the tube 31 has been shown whose anode 32 is supplied through an OR-gate 33 and two analogue gates 34 and 35, with the voltages $V_1$ and $V_2$ which enable it to selectively display the two phosphorescences, green and red, for example, which have not been shown on the screen 36 of the tube for reasons of simplification.

The computer 9 has its two inputs S and C respectively supplied from the two outputs of OR-gates 36 and 37. The threshold register 10 is connected to one of the inputs of the OR-gate 36 through the digital gate 38. The register 11 recording the contrast of the normal part of the image, which part will be called the region B and in which no special examination is being conducted, is connected by a logic gate 39 to a first input of the OR-gate 37.

The device is distinguished from that of the preceding figures by the presence of two comparators 131 and 132 connected to the output of the memory 4. These two comparators simultaneously acquire the logic state 1 when the output number from the memory is between $D - \epsilon$ and $D + \epsilon$, where D and $\epsilon$ are inroduced by two appropriate registers marked by a simple box 14.

The comparator 131 will be in the 1 state when the output number is less than or equal to $D + \epsilon$, and in the zero state when the contrary is the case. The comparator 132 will be in the 1 state when the output number N is greater than or equal to $D - \epsilon$, and in the zero state when the contrary is the case.

The outputs of these two comparators 131 and 132 are connected to the two inputs of an AND-gate 40. The output of the AND-gate 40 is connected directly to the control input of the AND-gate 35 and, through the medium of an inverter 41, to a control input of an AND-gate 34. It is also connected to the control input of a logic gate 42 and, through an inverter 43, to the input of a logic gate 38 and, finally, through an inverter 44, to the input of a logic gate 39.

It should be pointed that the term logic gate as used here, is intended to signify a device which supplied the number which it records when it receives an appropriate command from a control input, and that the term logic OR-gate as used here signifies register which, indiscriminately, supplies at its output the numbers applied to one of its inputs, it being understood of course that said inputs are never supplied simultaneously.

The device furthermore comprises a register 45 which is controlled by the register 14 and which is supplied with the number $\epsilon$. This register furnishes its output number to the logic gate 46 whose control input is connected to the output of the gate 40.

The operation of the system is as follows:

The operator, by means of the register 14, introduces into the comparators 131 and 132 numbers $D - \epsilon$ and $D + \epsilon$. If one of the two comparators 131 and 132 is in the "0" state, then the gate 40 is blocked. The inverter 41 opens the gate 34 and the voltage $V_1$ is applied to the anode 32 via the OR-gate 33. The screen of the tube acquires the colour green.

The inverters 43 and 44 acquire the "1" state and the threshold defined by the register 10 will be applied by the AND-gate 38 and the OR-gate 38, to the input S of the computer. Similarly, the contrast $C_B$ defined by the register 11 will be applied by the gate 39 and the OR-gate 37, to the input C of the computer. Everything will take place in the manner described in the case of the previous examples.

If, on the other hand, the two comparators 131 and 132 acquire the "1" state, the gate 40 will be open, the gate 34 closed, the gate 35 open and the voltage $V_2$ will be applied to the accelerating anode. The red phosphorus of the tube will be excited and it will be the region A which it is required to differentiate, which will appear in red upon the screen.

The register 14 supplies its contrast command to the register 45, the gate 40 opens the gate 46, and the gate 39 is closed by the inverter 44, and the number furnished by the register 45 is supplied to the input C of the computer.

Similarly, the threshold $D - \epsilon$ will be applied by the gate 42 to the input of the OR-gate 36 and applied to the input S of the computer, the gate 38 being closed by the inverter 43. At this instant, everything will take place as if the numbers $D - \epsilon$ and $C_A$ had been applied to the computer input, and the region A will appear with its own colour and contrast.

Figure 10:
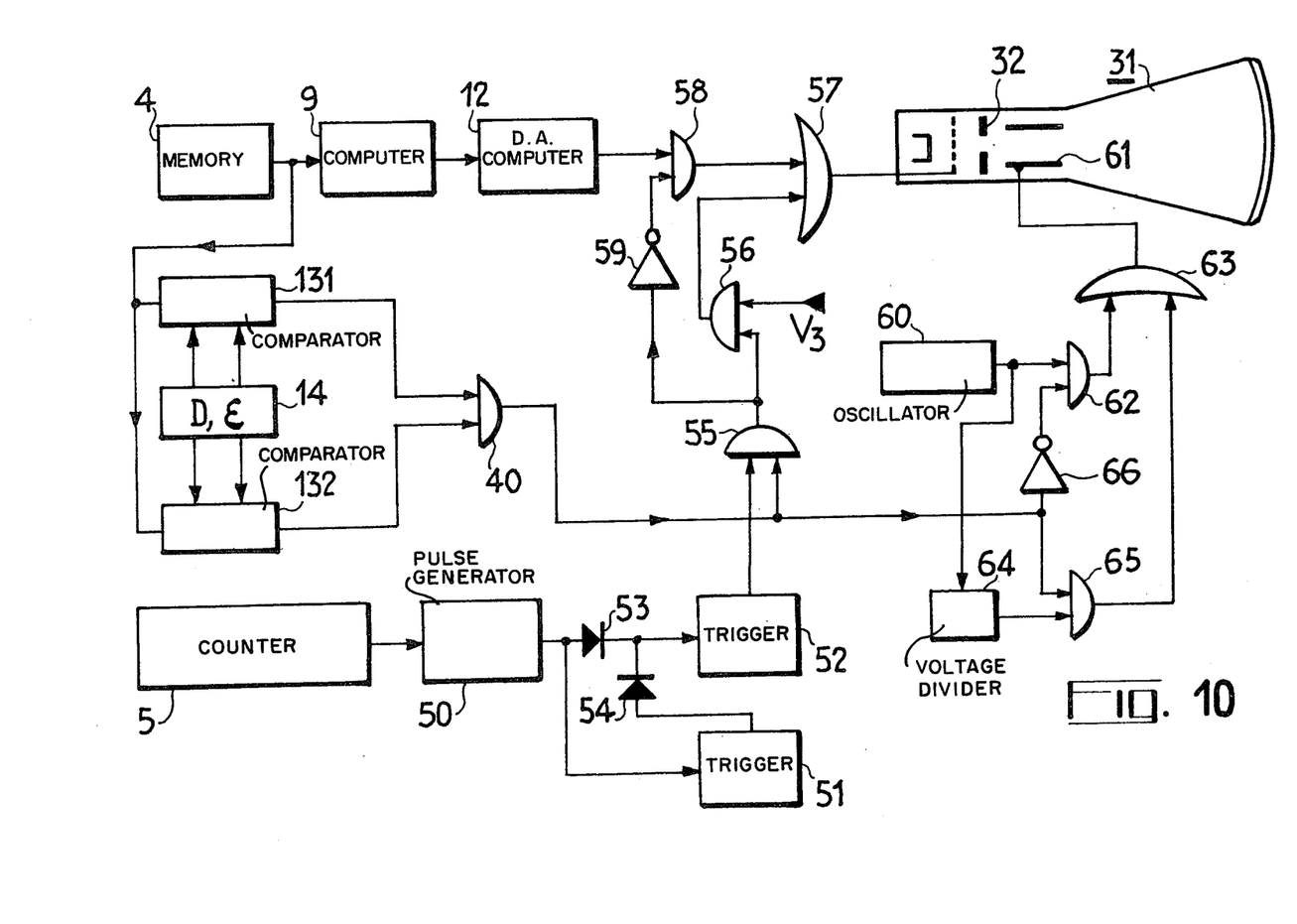

The invention opens up another possibility, which will be illustrated in FIG. 10. The region A which is to be specially examined, may be differentiated through the agency of the dimensions of the corresponding grid areas.

The device shown in FIG. 10 comprises, like that shown in FIG. 9, the register 14 which is capable of recording the data D and $\epsilon$, and the two comparators 131 and 132 which simultaneously acquire the "1" state when the number N leaving the memory is between $D - \epsilon$ and $D + \epsilon$. The two outputs of the comparators are connected to the AND-gate 40. The first set of elements controlled by the points counter 5, make it possible, for example, to reduce by half the horizontal dimension of the areas representing the grid areas whose opacities fall within the desired range. A second set of elements makes it possible in a similar way to reduce by half the vertical dimension of these areas. These two sets of elements, will be described successively.

The mesh counter 5 controls a pulse generator 50 which has the periodicity of the clock, namely, in order to give a concrete example, 1.6 microseconds. This pulse generator triggers a first monostable trigger stage 51 of relaxation time 1.2 microseconds. A second monostable trigger stage 52 of periodicity 0.4 microseconds is controlled directly by the pulse generator 50 and by the monostable trigger stage 51. Two diodes 53 and 54 connected in the manner indicated make it possible to prevent any reaction reaching the output of the monostable trigger stage 51, from its input.

An AND-gate 55 is supplied on the one hand with the output voltage from the monostable trigger stage 52 and on the other with the output voltage from the AND-gate 40. The output of the AND-gate 55 is in the "1" state when the output of the AND-gate 40 is in the "1" state and when the monostable trigger stage 52 is supplying its 1-level voltage.

The output of the AND-gate 55 opens an analogue gate 57 which is supplied at its other input with a direct voltage $V_3$ capable of blocking the modulating electrode of the tube 31.

This AND-gate 56 has its output connected to a first input of an OR-gate 57 whose output is connected to the modulating electrode.

The other input of the OR-gate 57 is connected through the medium of an AND-gate 58 of the digital-analogue converter 12 which supplies the data.

The other input of the gate 58 is connected by an inverter 59 to the output of the AND-gate 55.

The operation of this system is as follows. When the number N delivered by the memory 4 is outside the range, one of the two comparators 131 or 132 is in the "0" state, the output of the AND-gate 55 is in the "0" state, the output of the inverter 59 is in the "1" state and the gate 58 opens so that scanning of the screen takes place normally. In the case where N is between $D - \epsilon$ and $D + \epsilon$, the two comparators 131 and 132 are in the "1" state, the gate 40 is open and one of the inputs of the gate 55 is in the "1" state. The output pulses from the pulse generator 50 have the effect of triggering the monostable trigger stages 51 and 52.

The retriggering of the monostable trigger stage 52 by that 51, has the effect of placing the output of the monostable trigger stage 52 in the "1" state for 0.4 microseconds after the passage of the corresponding pulse, and of returning to the "1" state 0.4 microseconds before triggering by the next pulse occurs. The monostable trigger stage 52 is in the "1" state for an interval corresponding to half the periodicity of the pulses, and symmetrical in relation to the centre of said same period.

When its output is in the "1" state, it opens the gate 55 which in turn opens the gate 56. The voltage $V_3$ is applied to the modulating electrode and the tube extinguishes.

Line scanning is controlled by a high frequency oscillator 60 operating for example at 3 Me/sec so that each scanned line has a well-defined height, greater than that of the elementary spot. This oscillator acts upon the vertical defection circuit of the tube. The elements which will be now described, make it possible in respect of each of the selected grid areas, to reduce this height by half, the corresponding grid area being centred on the line scanned by the spot.

To this end, the oscillator 60 is connected to the deflection circuits 61 through an analogue gate 62 and an OR-gate 63. The control input of the gate 62 is connected to the gate 40 by an inverter 66. An A.C. voltage divider 64 is connected to the output of the oscillator 60 and produces at its own output a voltage such that the reduction in height referred to earlier, can be brought about. This circuit 64 is connected to a gate 65 whose control input is connected to the output of the gate 40. The output of the gate 65 is connected to the input of the OR-gate 63.

The operation of the system is very simple. If the gate 40 is closed, the gate 62 is opened by the inverter 66 and the oscillator 60 supplies its voltage to the system 61 through the OR-gate 63. The height of the meshes is normal.

If the gate 40 is open, the gate 65 is open and it is the voltage-device 64 which, through the OR-gate 63, supplies the scanning voltage. The desired result is achieved.

Figure 11:
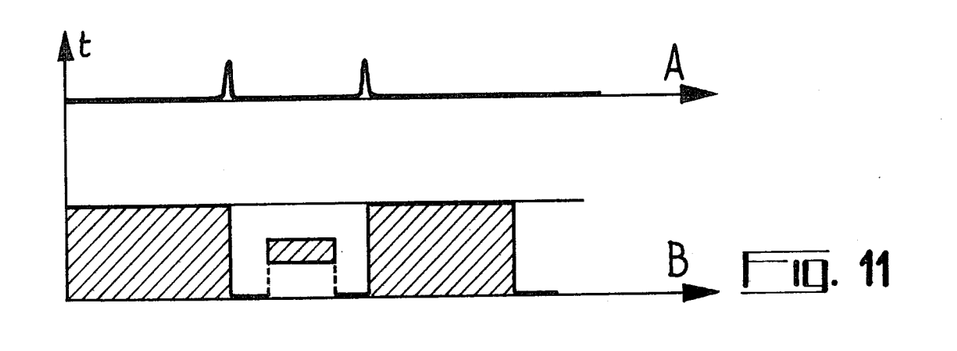

The assembly of these operations has been shown in FIG. 11, the FIG. 11A showing the sequence of the pulses, the FIG. 11B the line scanning and the reduction of the height and width of a mesh of the region by half.

Of course other methods of realisation can be envisaged without leaving the framework of the invention in particular the various elements described relating to the differentiation of the zones and the change of contrast can be combined.

What we claim:

1. In a display cathode ray tube apparatus, capable of displaying the image of a preselected plane section of a body, after irradiation of said body by penetrating radiations by means of meshes, each of which represents a mesh of said section, said latter being divided up into rows and columns, a control electrode in said tube for controlling the brilliance of each of said meshes as a function of the opacity towards said radiations, of the corresponding mesh of said section, comprising means connected to said control electrode, for selecting meshes whose brilliance is comprised between predetermined adjustable limits, means for adjusting said limits, and means connected to said control electrode, for differentiating the appearance of said selected meshes, from the remainder of said meshes, a data processing system containing said opacity data corresponding to said section and digital to analog converter means connected to said system for controlling said control electrode, a synchronising clock, controlling on the one hand the selection of the memory data corresponding to said selected section from said data processing system; a computer for receiving said data, and in response, furnishing numbers, each number representing a given range of opacities, a first digital to analog converter connected to said computer, whose output voltage controls the control electrode in said display tube, said clock also controlling a point counter, a line counter, second digital to analogue converter devices, connected to said counters, controlling the horizontal and the vertical scanning respectively of said tube, said computer having a first and a second input, a first register storing the number form which said control electrode blocks said tube and a second register controlling correspondence between luminosity of the mesh and the number transducing the corresponding opacity coefficient, said first and second registers controlling respectively first and second computer inputs, said selecting means including a comparator system having a first group of inputs connected to said computer output, and having respectively the state "0" and "1" corresponding to the number manifested by said storage device in the binary code, a second group of inputs, a register having its respective stages respectively connected to said second group of inputs, said stages having the states "0" and "1" corresponding respectively to the selected number in said code, a two state "0" and "1" output, said output taking the state "1" at the coincidence of said numbers, and a logic circuit connected to said output for controlling said control electrode.

2. An apparatus as claimed in claim 1, further comprising a d.c. supply, producing a d.c. voltage, and having connection means to said control electrode said voltage when applied to said control electrode, being outside the voltage limits, for which the tube is blocked on one side, or attains its maximum beam intensity on the other side, said logic circuit controlling said connection means, when said comparator output is at the "1" state.

3. An apparatus as claimed in claim 1, comprising a d.c. voltage source and an adder, said adder having its output connected to said control electrode, and two inputs having respectively first and second connecting means for connection to said digital to analog converter, output and to said d.c. voltage source output, said second connecting means being controlled by said logic circuit.

4. An apparatus as claimed in claim 3, further comprising a square wave voltage generator, controlled by said clock, and having a triggering input, said logic circuit being connected to said triggering input.

5. An apparatus as claimed in claim 1, wherein said comparator system comprises a storage device containing two numbers D and $\epsilon$, and a first comparator and a second comparator, connected respectively to said storage device, and to said computer outputs, said comparators having respectively two state "0" and "1" outputs, said comparator taking respectively the state "1" where the number manifested by the computer is lower than $D + \epsilon$, and higher than $D - \epsilon$, and AND gate having respective inputs connected to said two comparator outputs, and a logical circuit actuated by said AND gate, for controlling one electrode in said tube.

6. An apparatus as claimed in claim 5, wherein said one electrode is an accelerating anode, said tube having a first and a second phosphore screen, said first and second phosphore screens being excited respectively by first and second voltages applied to said anode, first and second d.c voltage source having respective connection to said anode, said logic circuit controlling said connection according its state.

7. An apparatus as claimed in claim 5, wherein said logic circuit controls according to its state the amplitude of the vertical dimension and the horizontal dimension of each mesh.

* * * * *